United States Patent [19]

Shoji et al.

[11] Patent Number: 5,636,983
[45] Date of Patent: Jun. 10, 1997

[54] LASER CUTTING APPARATUS

[75] Inventors: Shigeru Shoji; Hiroshi Horiuchi, both of Sendai; Kazuaki Hara, Kotobashi, all of Japan

[73] Assignee: The Yoshida Dental Mfg. Co., Ltd., Japan

[21] Appl. No.: 341,517

[22] Filed: Nov. 17, 1994

[30] Foreign Application Priority Data

Nov. 18, 1993 [JP] Japan ................... 5-312627

[51] Int. Cl.⁶ ................ A61C 1/00; A61C 3/02
[52] U.S. Cl. .................. 433/29; 433/88; 606/10
[58] Field of Search ............... 433/29, 88, 144, 433/215; 606/10, 11, 13, 14, 17, 18

[56] References Cited

U.S. PATENT DOCUMENTS 5,334,016  8/1994  Goldsmith et al. ............ 433/88 X
5,334,019  8/1994  Goldsmith et al. ............ 433/88

*Primary Examiner*—Robert P. Swiatek
*Assistant Examiner*—Elizabeth Shaw
*Attorney, Agent, or Firm*—Ostrolenk, Faber, Gerb & Soffen, LLP

[57] ABSTRACT

A laser cutting apparatus is disclosed which includes a laser emitter capable of outputting a laser beam in pulses, a laser beam irradiation member, and a dental-crown polishing and washing member. The dental-crown polishing and washing member has an injection member through which air, water and polishing material are output toward a laser-beam-irradiated surface. A control member is provided which is capable of controlling the operation of laser emitter and dental-crown polishing and washing member. The laser beam irradiation member and injection member are combined with each other by means of an adapter disposed therebetween, thereby enabling both of laser beam irradiation member and injection member to be held and operated by a single hand. By employing this laser cutting apparatus, a high-energy laser beam can be used in the medical and dental fields for removing soft dentin to form a cavity. This apparatus does not have problems due to irradiation of a high-energy laser beam, such as the production and residue of a carbonized layer in the dentin, formation of a fused layer in the dentin, occurrence of a cavity margin having an irregular configuration, and cracking and damaging of the dental pulp attributed to a temperature rise.

4 Claims, 2 Drawing Sheets

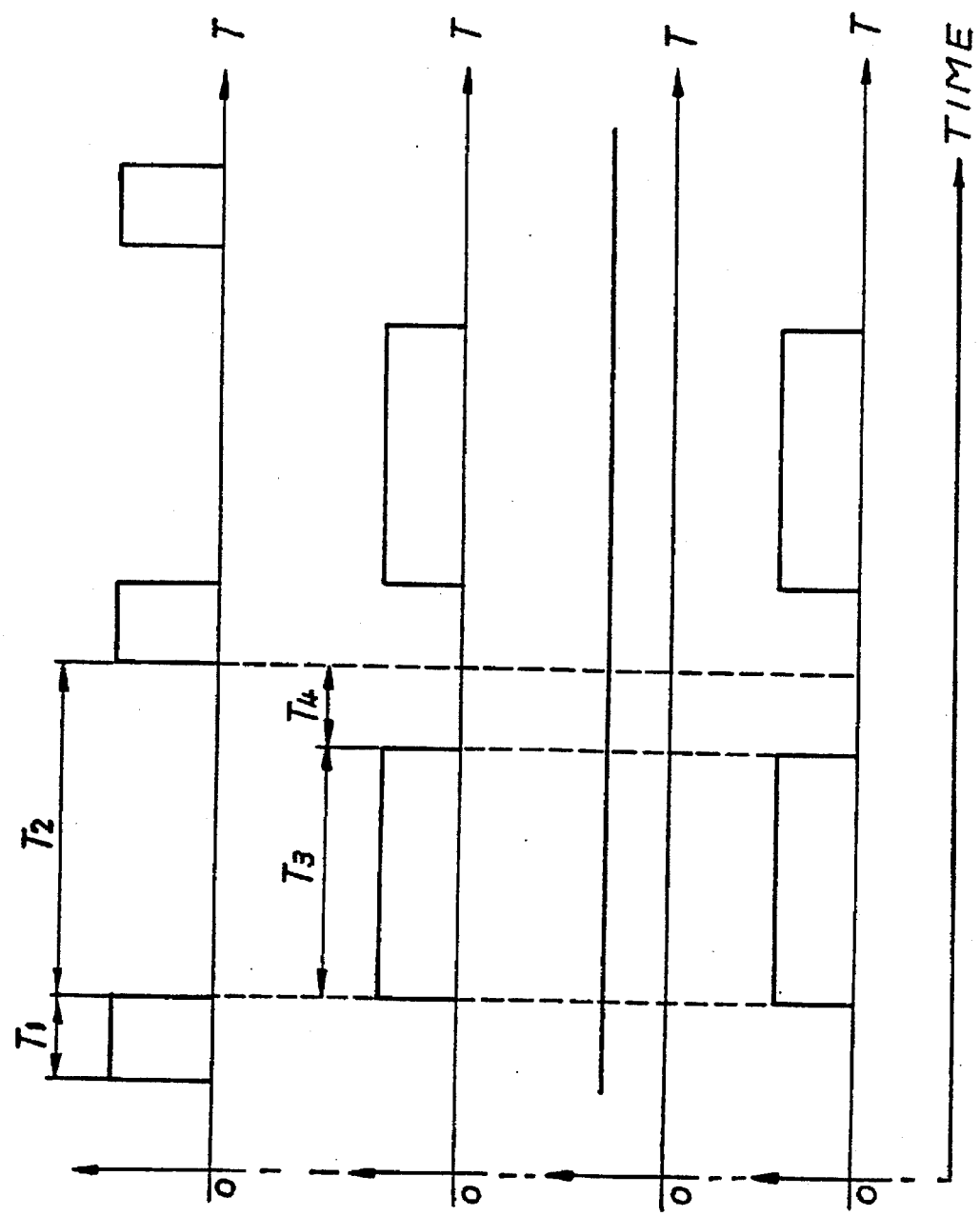

dental

LASER CUTTING APPARATUS

BACKGROUND OF THE INVENTION

1. Field Of The Invention

The present invention relates to a cutting apparatus employing a laser emitter, which is for use in medical and dental fields.

2. Discussion Of Related Art

Conventionally, with respect to a cutting apparatus employing a laser emitter which is for use in medical and dental fields, laser beam has experimentally been used for removing soft dentin.

However, it is known that, when laser beam is used in medical and dental fields for removing soft dentin to thereby form a cavity, problems due to the irradiation of high-energy laser beam occur such as production and leaving of a carbonized layer in the dentin, formation of a fused layer in the dentin, occurrence of a cavity margin having an irregular configuration, cracking and damaging of the dental pulp attributed to a temperature rise.

SUMMARY OF THE INVENTION

The inventors have made extensive and intensive studies with a view toward developing a laser cutting apparatus which solves the above-mentioned problems. As a result, it has unexpectedly been found that the above-mentioned problems can be successfully solved by a novel laser cutting apparatus in which a laser emitter is combined with a dental-crown polishing and washing member. The present invention has been completed on the basis of the above finding.

It is, therefore, an object of the present invention to provide a laser cutting apparatus free from the above drawbacks of the prior art.

The foregoing and other objects, features and advantages of the present invention will become apparent from the following detailed description and appended claims taken in connection with the accompanying drawings.

BRIEF DESCRIPTION OF THE DRAWINGS

In the drawings:

FIG. 2 is a timing chart showing one example of the timing of operations of the laser emitter and the dental-crown polishing and washing member during the operation of the laser cutting apparatus of the present invention.

DETAILED DESCRIPTION OF THE INVENTION

Figure 1:
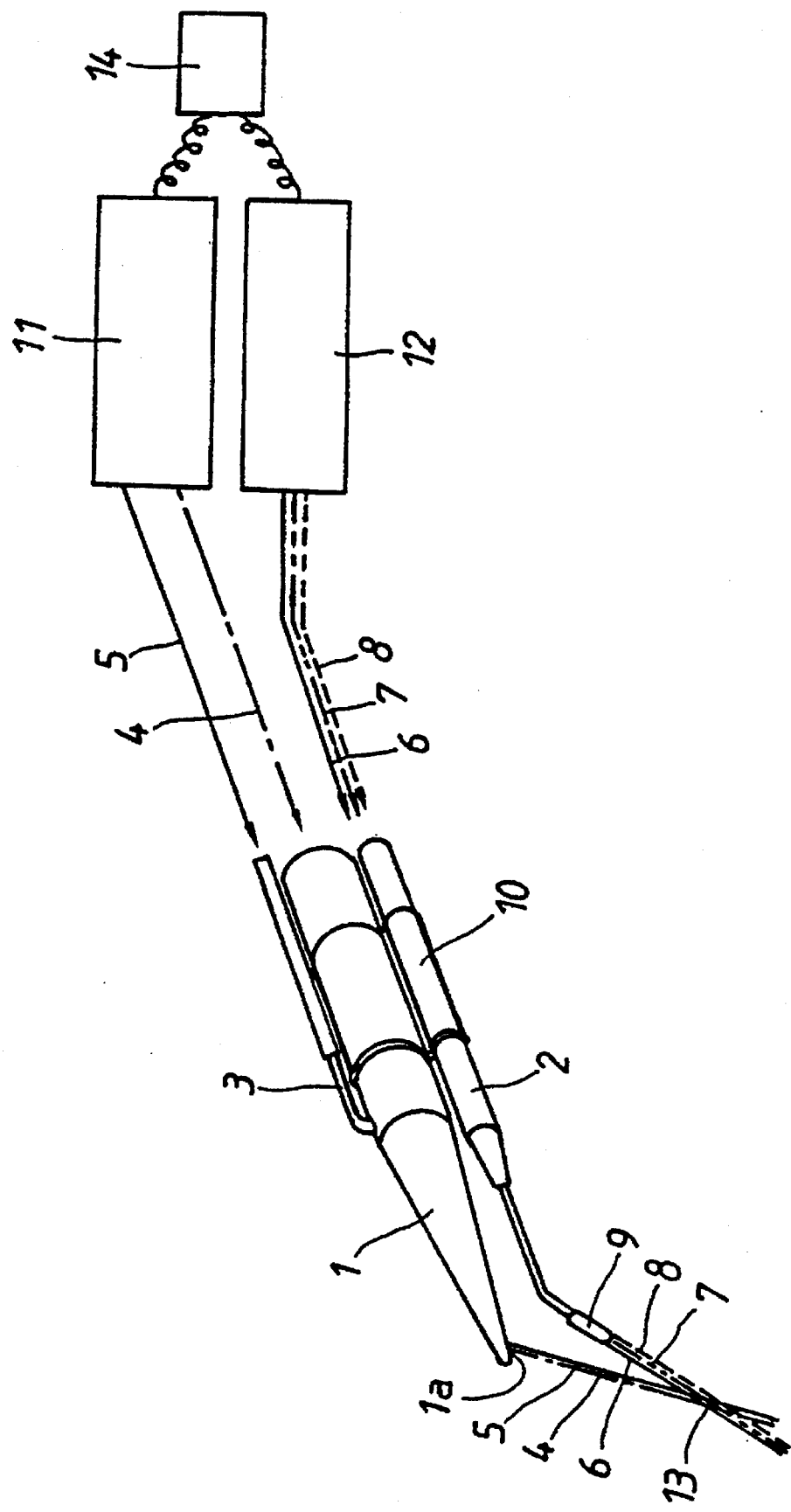
FIG. 1 is a diagrammatic view showing the construction of one form of the laser cutting apparatus according to the present invention.

For attaining the above objects, according to the present invention, there is provided a laser cutting apparatus for use in medical and dental fields for forming a cavity, comprising: a laser emitter capable of outputting laser beam continuously or in pulses, and a laser beam irradiation member; a dental-crown polishing and washing member capable of outputting air, water and a polishing material to a laser-beam-irradiated surface, and an injection member adapted to inject the output air, water and polishing material and connected to the dental-crown polishing and washing member; and a control member adapted to control the operations of the laser emitter and the dental-crown polishing and washing member, wherein the laser beam irradiation member and the injection member are combined with each other by means of an adapter disposed therebetween, thereby enabling both of the laser beam irradiation member and the injection member to be held and operated by a single hand.

In the laser cutting apparatus of the present invention, the control member is capable of commanding the laser emitter so that laser beam is output continuously or in pulses and so that the duration of each pulse and the intervals between the pulses are arbitrarily set when the laser beam is output in pulses; also capable of setting the output and the timing of operation of the dental-crown polishing and washing member so that the air, water and polishing material are injected during the intervals between the laser beam pulses; and further capable of memorizing set values of operation conditions of the laser emitter and the dental-crown polishing and washing member.

In the cutting apparatus of the present invention, when laser beam is output in pulses, a carbonized layer can be removed by means of a polishing material while avoiding a temperature rise by cooling the laser-beam-irradiated surface with water during the intervals between the pulses. Further, since the laser beam irradiation member and the injection member connected to the dental-crown polishing and washing member are combined with each other, both of these can be held by a single hand, thereby improving the efficiency of the operation.

DETAILED DESCRIPTION OF THE EMBODIMENTS

As shown in FIG. 1, laser beam irradiation member 1 has, on its side face, an inner inlet for laser beam (not shown) and inlet 3 for assist air 5 which is fed for preventing the clouding of a lens system for the convergence and refraction of the laser beam. The tip of laser beam irradiation member 1 is provided with outlet 1a through which high-energy laser beam 4 output from laser emitter 11, visible guide beam (not shown) indicating a laser-beam-irradiated part 4 and assist air 5 are passed.

On the other hand, one end of injection member 2 is provided with injection nozzle 9 for injecting air 6, polishing material 7 and water 8 each output from dental-crown polishing and washing member 12. Laser beam irradiation member 1 for laser beam 4 and injection member 2 are combined with each other by means of adapter 10 disposed therebetween to thereby enable both of them to be held by a single hand. Moreover, laser beam irradiation member 1 and injection member 2 are combined with each other while maintaining their relative positional relationship in a manner such that air 6, polishing material 7 and water 9 each injected from injection nozzle 9 also hit part 13 irradiated with laser beam 4 coming from laser beam irradiation member 1, and, in other words, in a manner such that injected air 6, polishing material 7 and water 9 intersect with laser beam 4 at laser-beam-irradiated part 13.

Control member 14 is electrically connected to each of laser emitter 11 and dental-crown polishing and washing member 12, which control member controls these on the basis of their mutual output relationships. Control member 14 is capable of commanding laser emitter 11 to output laser beam 4 continuously or in pulses. When laser beam 4 is output in pulses, control member 14 is capable of commanding laser emitter 11 so that the duration of each pulse and the intervals between the pulses are arbitrarily set.

Further, when laser beam 4 is output in pulses, control member 14 is capable of commanding dental-crown polishing and washing member 12 to inject air 6, water 8 and polishing material 7 during the intervals between the laser beam pulses. In addition, control member 14 can control the peak energy of irradiation laser beam 4. Further, control member 14 is capable of memorizing set values of the above operation conditions.

With respect to the operation of the laser cutting apparatus of the present invention, a carbonized material formed at the laser-beam-irradiated part 13 is removed by means of polishing material 7 while cooling the laser-beam-irradiated part 13, by injecting water 8 and polishing material 7 during the period of time $T_3$ indicated in the timing chart for injecting polishing material and water of FIG. 2, the $T_3$ corresponding to part of the irradiation pause interval $T_2$ indicated in the timing chart for outputting laser beam 4 of FIG. 2 in which laser beam irradiation pulse time $T_1$ and irradiation pause interval $T_2$ are alternately repeated. During the period of time $T_4$ corresponding to the remainder of irradiation pause interval $T_2$, water is blown off in preparation for the next irradiation by compressed air being constantly injected as indicated in the timing chart for air of FIG. 2.

The period of time $T_3$ in which the carbonized material is removed must be within the irradiation pause interval $T_2$. Thus, when the period of time $T_3$ must be changed for rendering the removal of the carbonized material satisfactory, this can be met by changing the irradiation pause interval $T_2$ in accordance with the period of time $T_3$ by means of the pulse control member 14, as mentioned above. Also, the peak energy of irradiation laser beam is adjusted to the level optimum for cavity formation.

In this embodiment, fine powder composed mainly of sodium bicarbonate as a polishing material was injected toward the laser-beam-irradiated part 13. Excellent polishing results were confirmed by observing the resultant polishing condition of the surface of the laser-beam-irradiated part 13.

Although the operation of dental-crown polishing and washing member 12 may be performed only with the use of compressed air, water is also preferably employed because water is effective in preventing the scattering of fine powder of sodium bicarbonate as a polishing material and in cooling the laser-beam-irradiated part.

As described hereinabove, in the laser cutting apparatus of the present invention, a laser beam irradiation member and a nozzle for injecting compressed air, water and a polishing material are combined with each other, so that not only is the cavity forming operation greatly facilitated, but also, when laser beam is output in pulses, a carbonized material can be removed while cooling the laser-beam-irradiated part during the intervals between the pulses with the result that the cutting apparatus of the present invention has resolved various drawbacks of the prior art due to the use of high-energy laser beam, such as production and leaving of a carbonized layer in the dentin, formation of a fused layer, occurrence of a cavity margin having an irregular configuration, cracking and damaging of the dental pulp attributed to a temperature rise.

What is claimed is:

1. A laser cutting apparatus for use in medical and dental fields for forming a cavity, comprising:

a laser emitter capable of outputting a laser beam continuously or in pulses, and a laser beam irradiation member;

a dental-crown polishing and washing member capable of outputting air, water and a polishing material to a laser-beam-irradiated surface, and an injection member adapted to inject the outputted air, water and polishing material and connected to the dental-crown polishing and washing member; and a control member adapted to control the operations of the laser emitter and the dental-crown polishing and washing member;

said laser beam irradiation member and said injection member are combined with each other by an adapter disposed therebetween, thereby enabling both the laser beam irradiation member and the injection member to be held and operated by a single hand.

2. The laser cutting apparatus according to claim 1, wherein said control member is capable of commanding said laser emitter so that the laser beam is outputted continuously or in pulses and so that the duration of each pulse and the intervals between the pulses are arbitrarily set when the laser beam is output in pulses; also capable of setting the output and the timing of operation of the dental-crown polishing and washing member so that the air, water and polishing material are injected during the intervals between the laser beam pulses; and further capable of memorizing set values of operation conditions of the laser emitter and the dental-crown polishing and washing member.

3. The laser cutting apparatus according to claim 1, wherein the adapter maintains a positional relationship between the laser beam irradiation member and the injection member so that the injected air, polishing material and water intersect a path of the laser beam emitted from the laser beam irradiation member.

4. A laser cutting apparatus for use in medical and dental fields for forming a cavity, comprising:

a laser emitter capable of outputting a laser beam continuously or in pulses, and a laser beam irradiation member;

a dental-crown polishing and washing member capable of outputting air, water and a polishing material to a laser-beam-irradiated surface, and an injection member adapted to inject the outputted air, water and polishing material and connected to the dental-crown polishing an washing member; and a control member adapted to control the operations of the laser emitter and the dental-crown polishing and washing member, said laser beam irradiation member and said injection member are combined with each other by an adapter disposed therebetween, thereby enabling both the laser beam irradiation member and the injection member to be held and operated by a single hand;

said control member is capable of commanding said laser emitter so that the laser beam is outputted continuously or in pulses and so that the duration of each pulse and the intervals between the pulses are arbitrarily set when the laser beam is outputted in pulses, said control member is also capable of setting the output and the timing of operation of the dental-crown polishing and washing member so that the air, water and polishing material are injected during the intervals between the laser beam pulses and, said control member is further capable of memorizing set values of operation conditions of the laser emitter and the dental-crown polishing and washing member.

* * * * *